US011525828B2

(12) United States Patent
Snider et al.

(10) Patent No.: US 11,525,828 B2
(45) Date of Patent: *Dec. 13, 2022

(54) TEST APPARATUS AND METHODS FOR ST2 CARDIAC BIOMARKER

(71) Applicant: Critical Care Diagnostics, Inc., San Diego, CA (US)

(72) Inventors: James V. Snider, San Diego, CA (US); Jillian Elizabeth Bender, Carlsbad, CA (US); Shrin P. Kuo, Carlsbad, CA (US); Roy A. Chung, Carlsbad, CA (US)

(73) Assignee: Critical Care Diagnostics, Inc., San Diego, CA (US)

( * ) Notice: Subject to any disclaimer, the term of this patent is extended or adjusted under 35 U.S.C. 154(b) by 773 days.

This patent is subject to a terminal disclaimer.

(21) Appl. No.: 16/441,400

(22) Filed: Jun. 14, 2019

(65) Prior Publication Data
US 2020/0035357 A1    Jan. 30, 2020

Related U.S. Application Data

(60) Continuation of application No. 16/127,456, filed on Sep. 11, 2018, now Pat. No. 10,325,682, which is a (Continued)

(51) Int. Cl.
*G01N 33/543* (2006.01)
*G16H 40/63* (2018.01)
(Continued)

(52) U.S. Cl.
CPC ....... *G01N 33/54387* (2021.08); *A61B 90/98* (2016.02); *G01N 33/5302* (2013.01);
(Continued)

(58) Field of Classification Search
CPC ....... G01N 33/54387; G01N 33/54388; G01N 2333/7155
See application file for complete search history.

(56) References Cited

U.S. PATENT DOCUMENTS 6,740,293 B1    5/2004 Deng
6,867,051 B1    3/2005 Anderson et al.
(Continued)

FOREIGN PATENT DOCUMENTS

CN    101614732 A    12/2009
CN    102830234    * 12/2012 ....... G01N 33/54387
(Continued)

OTHER PUBLICATIONS

U.S. Appl. No. 14/244,526, filed Apr. 3, 2014, Snider et al.
(Continued)

*Primary Examiner* — Gailene Gabel
(74) *Attorney, Agent, or Firm* — Fish & Richardson P.C.

(57) ABSTRACT

The technology described in this document can be embodied in a test strip for use in measuring a level of an ST2 cardiac biomarker in a blood plasma sample. The test strip includes a base, and a plurality of conjugates, wherein each conjugate includes a reporter group bound to a first antibody that binds to ST2. A conjugate pad disposed along a length of the base and is configured to hold the plurality of conjugates that bind with ST2 to produce conjugate-ST2 complexes. The conjugate pad is further configured to receive the blood plasma sample. The test strip also includes a plurality of second and third antibodies that bind to ST2, and the conjugate-ST2 complexes, respectively. The plurality of second antibodies are bound to a membrane in a test location and the plurality of third antibodies are bound to the membrane in a control location.

17 Claims, 10 Drawing Sheets

Related U.S. Application Data division of application No. 14/566,955, filed on Dec. 11, 2014, now Pat. No. 10,079,073.

(51) Int. Cl.

| | |
|---|---|
| *G01N 33/53* | (2006.01) |
| *G01N 33/558* | (2006.01) |
| *A61B 90/98* | (2016.01) |
| *G16H 10/40* | (2018.01) |
| *G16Z 99/00* | (2019.01) |

(52) U.S. Cl.
CPC ..... *G01N 33/54388* (2021.08); *G01N 33/558* (2013.01); *G16H 10/40* (2018.01); *G16H 40/63* (2018.01); *G16Z 99/00* (2019.02); *G01N 2333/7155* (2013.01)

(56) References Cited

U.S. PATENT DOCUMENTS

| | | | |
|---|---|---|---|
| 7,432,060 | B2 | 10/2008 | Lee |
| 7,655,415 | B2 | 2/2010 | Lee |
| 7,670,769 | B2 | 3/2010 | Lee |
| 7,871,781 | B2 | 1/2011 | Rundstrom |
| 7,985,558 | B2 | 7/2011 | Lee |
| 7,989,210 | B2 | 8/2011 | Lee |
| 7,998,683 | B2 | 8/2011 | Snider et al. |
| 8,090,562 | B2 | 1/2012 | Snider et al. |
| 8,420,785 | B2 | 4/2013 | Snider et al. |
| 8,530,173 | B2 | 9/2013 | Lee |
| 8,597,958 | B2 | 12/2013 | Lee |
| 8,617,825 | B2 | 12/2013 | Snider et al. |
| 8,734,769 | B2 | 1/2014 | Lee |
| 10,079,073 | B2 * | 9/2018 | Snider ............... G01N 33/5302 |
| 10,324,089 | B2 * | 6/2019 | Snider ................ G01N 33/558 |
| 10,325,682 | B2 * | 6/2019 | Snider .................... G16Z 99/00 |
| 2002/0004019 | A1 | 1/2002 | Badtand et al. |
| 2002/0146346 | A1 | 10/2002 | Konecke |
| 2003/0124624 | A1 | 7/2003 | Tominaga |
| 2007/0020768 | A1 | 1/2007 | Rundstrom et al. |
| 2007/0266777 | A1 | 11/2007 | Bergman |
| 2009/0286692 | A1 | 11/2009 | Wainwright et al. |
| 2009/0305265 | A1 | 12/2009 | Snider et al. |
| 2009/0311805 | A1 * | 12/2009 | Bergman ............. G01N 33/558 422/68.1 |
| 2010/0009356 | A1 | 1/2010 | Snider et al. |
| 2010/0055683 | A1 | 3/2010 | Snider et al. |
| 2011/0053170 | A1 | 3/2011 | Snider et al. |
| 2011/0256635 | A1 | 10/2011 | Snider |
| 2012/0040381 | A1 | 2/2012 | Snider et al. |
| 2012/0065897 | A1 | 3/2012 | Snider et al. |
| 2012/0107851 | A1 | 5/2012 | Killard |
| 2012/0276551 | A1 | 11/2012 | Snider |
| 2012/0282634 | A1 | 11/2012 | Hughes et al. |
| 2013/0071404 | A1 | 3/2013 | Snider et al. |
| 2013/0177931 | A1 | 7/2013 | Snider et al. |
| 2013/0244236 | A1 | 9/2013 | Snider et al. |
| 2013/0273562 | A1 | 10/2013 | Lee |
| 2013/0317030 | A1 | 11/2013 | Lee |
| 2013/0345805 | A1 | 12/2013 | Snider et al. |
| 2014/0045200 | A1 | 2/2014 | Snider et al. |
| 2014/0051773 | A1 | 2/2014 | Snider |
| 2014/0058743 | A1 | 2/2014 | Snider et al. |
| 2015/0072022 | A1 | 3/2015 | Kiefer |
| 2015/0293085 | A1 * | 10/2015 | Anderberg ......... G01N 33/6893 506/18 |
| 2016/0011188 | A1 | 1/2016 | Anderberg |
| 2016/0169879 | A1 | 6/2016 | Snider |
| 2020/0041507 | A1 * | 2/2020 | Snider .................. G01N 33/566 |

FOREIGN PATENT DOCUMENTS

| | | |
|---|---|---|
| CN | 202735352 | 2/2013 |
| CN | 103154027 A | 6/2013 |
| CN | 103257225 | 8/2013 |
| CN | 103439519 A | 12/2013 |
| CN | 203502418 | 3/2014 |
| CN | 203759015 | 8/2014 |
| EP | 1033575 | 9/2000 |
| EP | 1186889 | 3/2002 |
| RU | 2007147939 2007147939 | 6/2009 |
| WO | WO 2011/127412 | 10/2011 |
| WO | WO 2014/070935 | 5/2014 |
| WO | WO 2016/094761 | 6/2016 |

OTHER PUBLICATIONS

U.S. Appl. No. 14/267,487, filed May 1, 2014, Snider.
www2.wpro.who.ine [online]. How To Do the Rapid Test for Malaria, dated Aug. 17, 2009 [retrieved on May 30, 2018], Retrieved from the Internet: URL <http://www2.wpro.who.int/NR/rdonlyres/D76666F7-5BF8-453F-9DA8-3EB4A9056CD6/0/GenericPllobAid_Final_lowRES.pdf> 1 page.
Brint et al., "ST2 is an inhibitor of interleukin 1 receptor and Toll-like receptor 4 signaling and maintains endotoxin tolerance," Nat. Immunol., 5(4):373-379 (2004).
Bruneau, "Selective changes in natriuretic peptide and early response gene expression in isolated rat atria following stimulation by stretch or endothelin-1," Cardiovasc. Res., 28(10):1519-1525 (1994).
Chinese Office Action in Application No. 201580074887.1, dated Jun. 28, 2018, 14 pages (with English translation).
European Search Report Application No. 15866534,9, dated Apr. 13, 2018, 15 pages.
Extended European Search Report in Application No. 15866534.9, dated Jul. 4, 2018, 16 pages.
GenBank Acc. No. NM_003856.2; Jan. 24, 2003.
GenBank Acc. No. NM_016232.4; Jan. 24, 2003.
GenBank Acc. No. NP_003847.2; Jan. 24, 2003.
GenBank Acc. No. NP_057316.3; Jan. 24, 2003.
GeneID: 9173; Aug. 21, 2008.
International Preliminary Report on Patentability in Application No. PCT/US2015/065176, dated Jun. 13, 2017.
International Search Report & Written Opinion; PCT/US2015/065176; dated Feb. 23, 2016; 14 pp.
Januzzi et al., "Utility of amino-terminal pro-brain natriuretic Peptide testing for prediction of 1-year mortality in patients with dyspnea treated in the emergency department," Arch. Intern. Med., 166(3):315-320 (2006).
Kieser et al.; "Identification of the Primary Growth Response Gene, ST2/T1, as a Gene Whose Expression is Differentially Regulated by Different Protein Kinase C Isozymes"; FEBS Lett. 372(2-3): 189-93; 1995.
Kumar et al.; "ST2/T1 Protein Functionally Binds to Two Secreted Proteins from Balb/c 3T3 and Human Umbilical Vein Endothelial Cells but Does Not Bind Interleukin 1*"; J. Biol. Chem. 270(46):27905-13; 1995.
Kuroiwa, et al.; "Construction of ELISA System to Quantify Human ST2 Protein in Sera of Patients"; Hybridoma 19(2):151-9; 2000.
MIM ID #601203, Aug. 21, 2008.
RU Decision To Grant in Russian Appln. No. 2017124329/04, dated Sep. 17, 2019, 20 pages (with English translation).
Sanada, et al.; "IL-33 and ST2 Comprise a Critical Biomechanically Induced and Cardioprotective Signaling System"; The Journal of Clinical Investigation; May 10, 2007; 12 pp.
Sanchez-Mas, et al.; "Modulcation of IL-33/ST2 System in Postinfraction Heart Failure: correlation with Cardiac Remodeling Markers"; European Journal of Clinical Investigation; vol. 44; 2014; pp. 643-651.
Schmitz et al., "IL-33, an interleukin-1-like cytokine that signals via the IL-1 receptor-related protein ST2 and induces T helper type 2-associated cytokines," Immunity, 23(5):479-490 (2005).
Seki, et al.; "Interleukin-33 Prevents Apoptosis and Improves survival After Experimental Myocardial Infarction Through ST2 Signaling"; American Heart Association; Feb. 16, 2010; 17 pp.
Shimpo et al., "Serum levels of the interleukin-1 receptor family member ST2 predict mortality and clinical outcome in acute myocardial infarction" Circulation, 109(18):2186-2190 (2004).

(56) References Cited

OTHER PUBLICATIONS

Tominaga, et al.; Nucleotide Sequence of a Complementary DNA for Human ST@; Biochim. Biophys. Acta; 1171:215-218; 1992.
Tominaga; A Putative Protein of a Growth Specific cDNA from BALB/c-3T3 Cells is Highly Similar to the Extracellular Portion of Mouse Interleukin 1 Receptor; FEBS Letters; Dec. 1989; vol. 258, No. 2, pp. 301-304; 4 pp.
UniGene No. Hs.66, Aug. 2, 2008.
Vivid™ Plasma Separation membrane; PALL Life Sciences; www.pall.com/oem; 2009; 6 pp.
Weinberg et al., "Expression and regulation of ST2, an interleukin-1 receptor family member, in cardiomyocytes and myocardial infarction," Circulation, 106(23):2961-2966 (2002).
Weinberg et al., "Identification of semm soluble ST2 receptor as a novel heart failure biomarker," Circulation, 107(5):721-726 (2003).
Written Opinion in Singapore Application No. 11201704679T, dated May 11, 2018, 9 pages.
Yanagisawa, et al.; Murine ST2 Gene is a Member of the Primary Response Gene Family Induced by Growth Factors; FEBS Lett. 302(1):51-3; 1992.
IN Office Action in Indian Appln. No. 201717020049, dated Nov. 12, 2021, 8 pages.
MX Office Action in Mexican Appln. No. MX/a/2017/007617, dated Jul. 15, 2021, 8 pages (with English translation).
CN Office Action in Chonese Appln. No. 20191080637.5, dated Jun. 8, 2022, 19 pages (with English translation).

\* cited by examiner

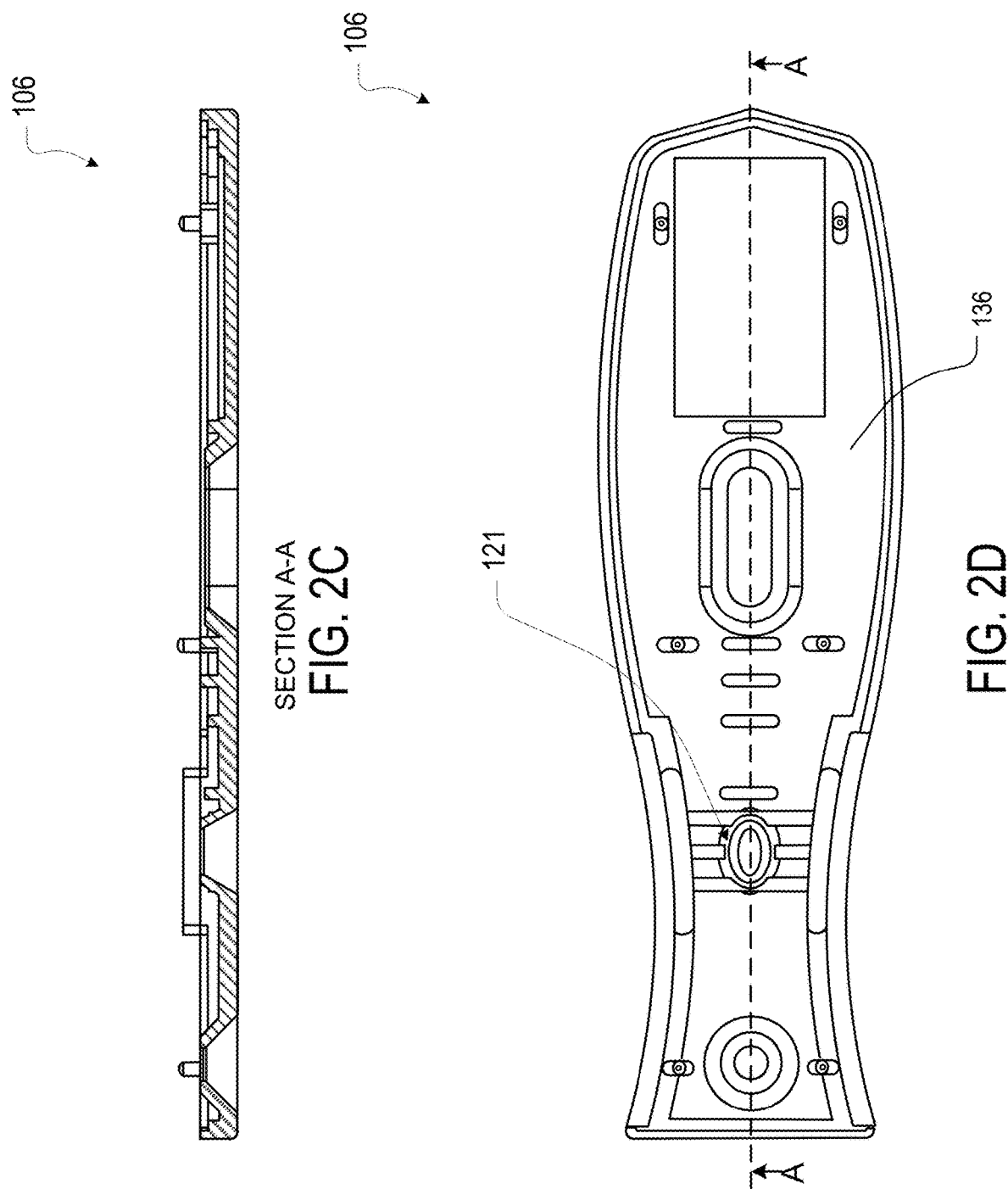

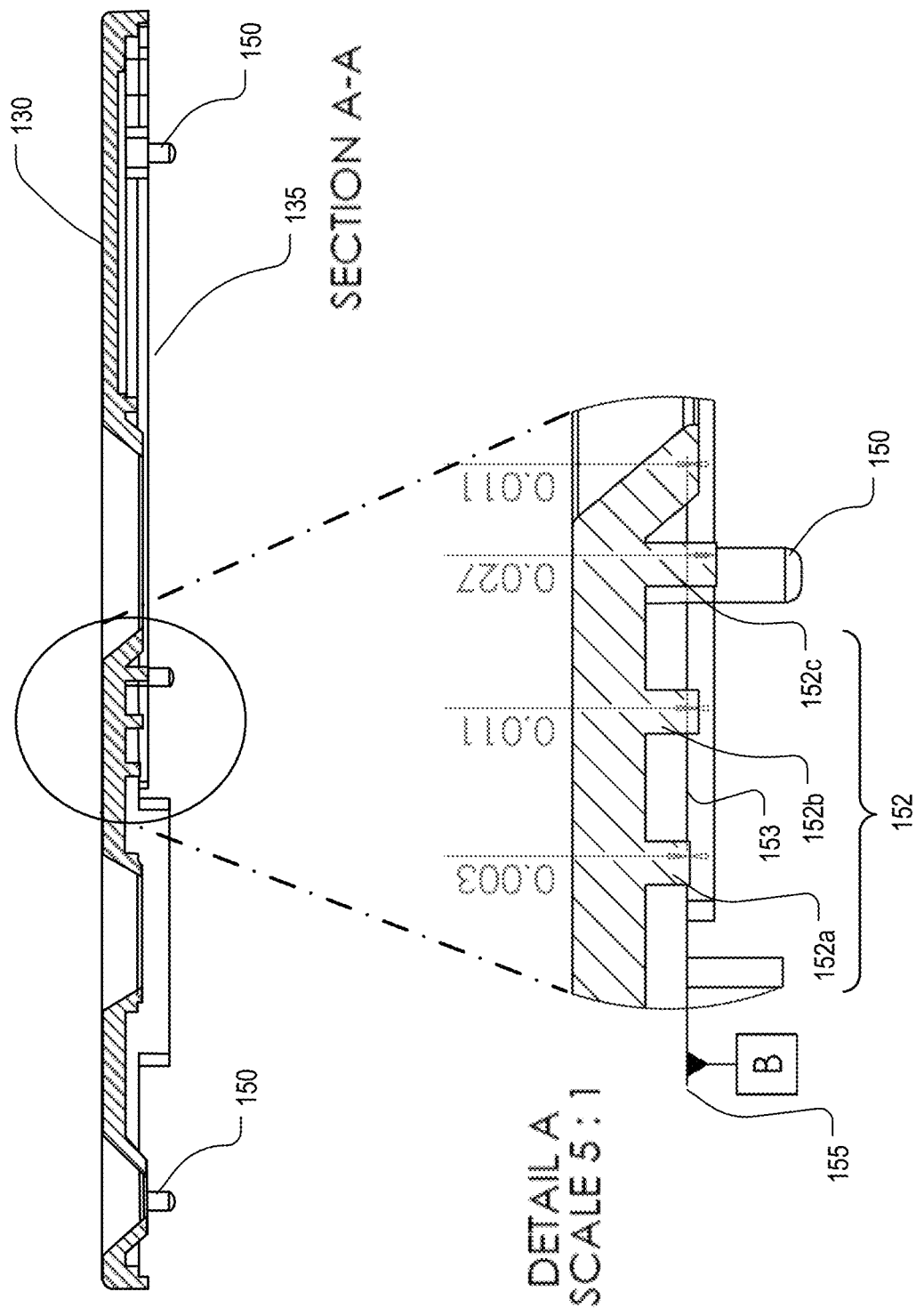

TEST APPARATUS AND METHODS FOR ST2 CARDIAC BIOMARKER

CLAIM OF PRIORITY

This application is a continuation of U.S. patent application Ser. No. 16/127,456, filed on Sep. 11, 2018, which is a divisional application of U.S. patent application Ser. No. 14/566,955, filed on Dec. 11, 2014, now U.S. Pat. No. 10,079,073, the entire contents of which are hereby incorporated by reference.

TECHNICAL FIELD

The invention relates to detecting the presence of cardiac biomarkers in blood.

BACKGROUND

Biomarkers that indicate a subject's likelihood of being afflicted by corresponding health-related condition significantly enhance a physician's ability to make informed treatment decisions.

Tominaga, FEBS Lett. 258:301-304 (1989), describes the isolation of murine genes that were specifically expressed by growth stimulation in BALB/c-3T3 cells; they termed one of these genes "St2" (for Growth Stimulation-Expressed Gene 2). The St2 gene encodes two protein products: ST2, which is a soluble secreted form; and ST2L, a transmembrane receptor form that is very similar to the interleukin-1 receptors. The HUGO Nomenclature Committee designated the human homolog, the cloning of which was described in Tominaga et al., Biochim. Biophys. Acta. 1171:215-218 (1992), as Interleukin 1 Receptor-Like 1 (IL1RL1). The two terms are used interchangeably herein.

The ST2 gene is a member of the interleukin-1 receptor family, whose protein product exists both as a trans-membrane form, as well as a soluble receptor that is detectable in serum (Kieser et al., FEBS Lett. 372(2-3):189-93 (1995); Kumar et al., J. Biol. Chem. 270(46):27905-13 (1995); Yanagisawa et al., FEBS Lett. 302(1):51-3 (1992); Kuroiwa et al., Hybridoma 19(2):151-9 (2000)). ST2 was described to be markedly up-regulated in an experimental model of heart failure (Weinberg et al., Circulation 106(23):2961-6 (2002)) and this observation was validated in more recent work published by Pascual-Figal, et al. (2014). Analysis of clinical study cohorts shows that ST2 concentrations may be elevated in those with chronic severe heart failure (HF) (Weinberg et al., Circulation 107(5):721-6 (2003)) as well as in those with acute myocardial infarction (MI) (Shimpo et al., Circulation 109(18):2186-90 (2004)) and that this elevated concentration is clinically meaningful.

The trans-membrane form of ST2 is thought to play a role in modulating responses of T helper type 2 cells (Lohning et al., Proc. Natl. Acad. Sci. USA, 95(12):6930-5 (1998); Schmitz et al., Immunity 23(5):479-90 (2005)), and may play a role in the development of tolerance in states of severe or chronic inflammation (Brint et al., Nat. Immunol. 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., Cardiovasc. Res. 28(10):1519-25 (1994)), and has been shown to be involved in the cardiac remodeling process (Sanada, 2007; Seki, 2009)

SUMMARY

This disclosure describes test kits and apparatus for detecting whether a level of ST2 present in a human subject exceeds a threshold condition. The test strips include multiple antibodies that interact with one another or with the ST2 if present in a sample, e.g., a blood sample, to provide an indication of the level of ST2 in the sample. The flow of the sample within the test strips is assisted by a suitably formulated buffer. The test strips are disposed within specially designed housings to form cassettes, the interior of which is configured to create consistent support of the strip that aids the flow of the sample and the buffer along the test strip.

In one aspect, this document features test strips for use in measuring a level of an ST2 cardiac biomarker in a blood plasma sample. The test strips include a base, and a plurality of conjugates, wherein each conjugate includes a reporter group bound to a first antibody that binds to ST2. Each test strip further includes a conjugate pad disposed along a length of the base and configured to hold the plurality of conjugates that bind with ST2 to produce conjugate-ST2 complexes, wherein the conjugate pad is further configured to receive the blood plasma sample. The test strip also includes a plurality of second antibodies that bind to ST2, and a plurality of third antibodies that bind to the conjugate-ST2 complexes. A membrane is disposed on the base such that the membrane is in fluid communication with the conjugate pad. The plurality of second antibodies are bound to the membrane in a test location and the plurality of third antibodies are bound to the membrane in a control location arranged further from the conjugate pad than the test location.

In another aspect, this document features test devices that include a test strip having a first end and an opposite second end, and a housing for the test strip and a radio frequency identification (RFID) tag configured to store information associated with the test strip, a first section, and a second section. The first section includes an outer face and an inner face, wherein the inner face of the first section comprises a channel to receive the test strip along the length of the first section. The second section includes an outer face and an inner face, wherein the second section is configured to be attached to the first section such that in an attached configuration the inner face of the first section faces the inner face of the second section, and the first and second sections together enclose the RFID tag and the test strip within the housing. The second section includes a buffer port configured to allow a buffer solution to be dispensed to a portion of the test strip proximate to a first end of the test strip, a test window configured to facilitate imaging of one or both of a test location and a control location on the test strip, and a sample port disposed between the buffer port and the test window. The sample port is configured to enable a sample of blood plasma to be dispensed to the test strip. The second section also includes a set of projections disposed on the inner face of the second section between the test window and the sample port such that in the attached configuration, wherein each projection in the set of projections is in contact with the test strip. A height of at least one projection in the set of projections is different from a height of another projection in the set of projections, and heights of the different projections are configured such that, in the attached configuration, the set of projections produces a pressure gradient that allows a fluid to flow at a predetermined flow rate along the length of the test strip between the first and last projections in the set of projections.

In another aspect, this document features test systems for ST2 cardiac biomarker. The test systems include a test strip, a housing for the test strip, an identification tag, and a reader device. The test strip is configured to facilitate detection of a threshold level of ST2 in blood plasma. The housing includes a first section that includes an outer face and an inner face, wherein the inner face of the first section includes a channel to receive the test strip along the length of the first section. The second section includes an outer face and an inner face, wherein the second section is configured to be attached to the first section such that in an attached configuration the inner face of the first section faces the inner face of the second section. The first and second sections together enclose the test strip within the housing. The second section includes a buffer port configured to allow a buffer solution to be dispensed to a portion of the test strip proximate to a first end of the test strip, a test window configured to facilitate imaging of one or both of a test location and a control location on the test strip, and a sample port disposed between the buffer port and the test window. The sample port configured to enable a sample of blood plasma to be dispensed to the test strip. The second section also includes a set of projections disposed on the inner face of the second section between the test window and the sample port such that in the attached configuration, each projection in the set of projections is in contact with the test strip. A height of at least one projection in the set of projections is different from a height of another projection in the set of projections, and heights of the different projections are configured such that, in the attached configuration, the set of projections produces a pressure gradient that allows a fluid to flow at a predetermined flow rate along the length of the test strip between the first and last projections in the set of projections. The reader device is configured to accept at least a portion of the housing within the reader. The identification tag is disposed on or within the housing, wherein the identification tag is configured to store information associated with the test strip. The reader device includes an optical system that images one or both of the test location and the control location on the test strip, and displays an estimated level of ST2 in the sample of blood plasma.

Implementations of the above aspects can include one or more of the following.

Either or both of the first or the second antibodies can bind specifically to ST2. The test strip can include an absorbent pad disposed on the base, and in fluid communication with the membrane at an end or side of the membrane opposite the conjugate pad. The absorbent pad can be configured to absorb plasma and buffer that has traversed through the membrane. The conjugate pad can be disposed on the base to receive a buffer solution. The conjugate pad can include glass and/or polyester fibers. At least one of the plasma separation pad or the membrane can include nitrocellulose. The first antibodies can include monoclonal antibodies. The reporter group can include fluorescent particles. The monoclonal antibodies can include 7E4-monoclonal-anti-ST2 antibodies that are conjugated to fluorescent particles. The second antibodies can include 9F8-monoclonal-anti-ST2 antibodies. The third antibodies can include Goat anti-Mouse IgG antibodies. The second antibodies may change in appearance depending on an amount of the bound conjugate present in the blood plasma traversing the first portion.

The predetermined flow rate can be such that the fluid flows from the portion of the test strip adjacent to the buffer port of the second section to the portion of the test strip adjacent to the test window of the second section in about 20 minutes. The set of projections can be a set of ridges. The distances between ridges can be substantially equal. The set of projections can include four ridges. A first ridge can be disposed closer to the sample port than the other ridges, a fourth ridge can be disposed closer to the test window than the other ridges, and a second ridge and a third ridge can be disposed between the first and third ridges. The first section can include multiple attachment projections that are configured to attach to corresponding attachment receptacles disposed on the second section, wherein dimensions of the attachment projections and attachment receptacles are configured such that in the attached configuration, the set of projections produces the pressure gradient that allows the fluid to flow at the predetermined flow rate along the length of the test strip. The reader device can be configured to query the identification tag to obtain at least a portion of the stored information.

The technologies described herein provide a number of advantages. For example, the new methods and devices can be used to determine whether a patient should be admitted or held as an inpatient for further assessment, regardless of whether a definitive diagnosis has been made. Risk stratification based on ST2 level of a given subject can be facilitated, e.g., to make decisions regarding the level of aggressiveness of treatment that is appropriate for the subject. Better treatment decisions can be made, which in turn can lead to reduced morbidity and mortality, and better allocation of health care resources.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 2C is a side view of an example of a top portion of the ST2 detection apparatus.

FIG. 2D is a view of the inside face of the top portion of FIG. 2C.

FIG. 2E is a cross sectional view of an example of a top portion, together with a blown-up view of the projections.

DETAILED DESCRIPTION

Clinical evaluation of patients, particularly patients with non-specific symptoms such as dyspnea or chest pain, is often challenging. The cardiac biomarker ST2 can be used in prognostic evaluation of patients, regardless of the underlying cause of their disease. In some cases, the level of ST2 in blood can be a powerful indicator of cardiac health, and such information may be used in taking measures to prevent the onset of acute conditions or even death. The ST2 test apparatus described herein allows fast and reliable detection of ST2 levels in blood, which can then be used by physicians and clinicians to determine the best treatment plan for the patient.

The mRNA sequence of the shorter, soluble isoform of human ST2 can be found at GenBank Acc. No. NM_003856.2, and the polypeptide sequence is at GenBank Acc. No. NP_003847.2; the mRNA sequence for the longer form of human ST2 is at GenBank Acc. No. NM_016232.4; the polypeptide sequence is at GenBank Acc. No. NP_057316.3. Additional information is available in the public databases at GeneID: 9173, MIM ID #601203, and UniGene No. Hs.66. In general, the methods, devices, and systems described herein measure the soluble form of the ST2 polypeptide.

Figure 1A:
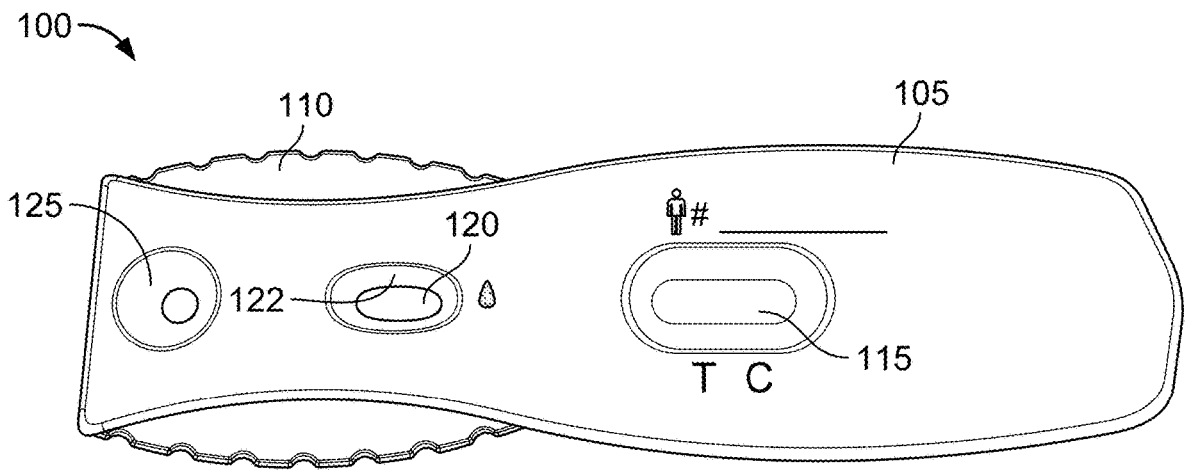
FIG. 1A is a top view of an example of an ST2 detection apparatus.
Figure 1B:
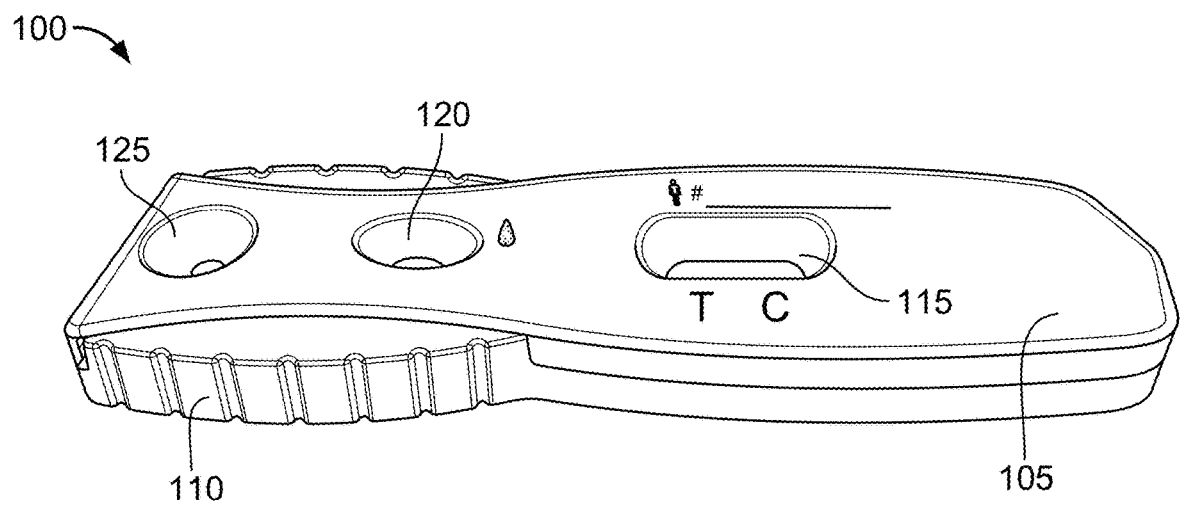
FIG. 1B is a perspective view of an example of an ST2 detection apparatus.

FIGS. 1A and 1B show top and perspective views of an example of an ST2 detection apparatus 100. In some implementations, the apparatus 100 includes a top portion 105 that is attached to a bottom portion 110. The top portion 105 and the bottom portion 110 together form a housing (also referred to as a cassette) within which an ST2 detection test strip is disposed. In some implementations, the top portion 105 includes a test window 115. The test window 115 is an opening or hole in the top portion 105 that exposes a portion of the test strip disposed in the housing. The portion of the test strip exposed by the test window 115 includes one or more marker locations that change appearance during the ST2 detection test. For example, the marker locations can include a control line (a location of which can be marked by the letter "C") that indicates that a test has been properly conducted, and a test line (a location of which can be marked by the letter "T") that becomes visible if a particular biomarker (e.g., ST2) is present in the analyte. The shape and dimensions of the test window 115 can be configured such that each of the marker locations is visible through the test window 115.

The top portion 105 also includes a sample port 120 through which the analyte (e.g., blood or other body fluid) is dispensed into the apparatus 100. The sample port 105 is an opening or hole in the top portion 105 that allows the analyte to be dispensed on sample-receiving portion of the test strip disposed in the housing. The shape and dimensions of the sample port are configured in accordance with the sample-receiving portion of the test strip. In some implementations, the sample port 120 includes a sidewall 122 that can form a seal with the sample-receiving portion of the test strip. In such a sealing configuration, the sidewall 122 inhibits lateral flow of a sample dispensed into the sample port 120 along the top of the test strip.

The top portion also includes a buffer port 125 through which a buffer solution can be dispensed into the apparatus 100. The buffer solution flows through the test strip, e.g., by capillary action, from the location beneath the buffer port 125 in the direction of the test window 115. As the buffer solution flows along within the test strip, the solution provides mobility to the plasma from the blood sample such that the plasma also flows along within the test strip from the location beneath the sample port 120 towards the test window 115. As the plasma flows past the portion of the test strip exposed by the test window 115, one or more of the marker locations (e.g., the test line and the control line) may change in their visual appearance depending on the level of ST2, if any, in the plasma. For example, if the level of ST2 in the plasma is above a threshold level, the marker locations corresponding to both the test line and the control line change appearance and both lines become visible. On the other hand, if the level of ST2 in the plasma is below the threshold level, only the marker location corresponding to the control line changes appearance and hence the control line (and not the test line) becomes visible. The lack of a control line can indicate that the plasma has not flowed through the test strip all the way to the control line, and the test is invalid.

In some implementations, in lieu of (or in addition to) a visual determination, the level of ST2 in the plasma can be measured quantitatively. In such cases, the housing or cassette can be configured to be inserted into a reader device (e.g., the reader device described below with reference to FIGS. 7A and 7B) that analyzes the test strip and provides a quantitative measure of the level of ST2 in the plasma. In some implementations, the reader analyzes the test strip through the test window 115 (for example, by obtaining an image of the portion of the test strip exposed at the test window 115). In some implementations, cassettes that are inserted into a reader may include an opening through which the test strip can be extricated from the cassette by the reader for analysis.

In some implementations, the level of ST2 can be performed, for example, by analyzing an image of the test line and the control line. In some implementations, such image analysis can be performed, for example, using an application installed on a computing device such as a laptop or desktop computer or a mobile device such as a smart phone or tablet. In some implementations, a user may be able to capture an image of the test line and control line using, for example, a camera of a mobile device. The captured image can then be analyzed, for example, using an application installed on the mobile device. In some cases, the captured image can also be analyzed by providing the image to a remote computing device that executes a suitable image analysis application.

In some implementations, the top portion 105 includes a designated portion for marking the cassette with identification information related to the corresponding subject or patient. In some implementations, the housing or cassette can also include an automatic identification module such as a radio frequency identification (RFID) tag encoded with the identification information related to the corresponding sample or patient. In such cases, the reader includes a suitable module for querying and retrieving information from the automatic identification module. For example, if the cassette includes an RFID tag, the receiver can be configured to include an RFID reader to retrieve information from the tag. Other suitable communication technologies such as near-field communications (NFC) or Bluetooth® can also be used in place of RFID.

Figure 2A:
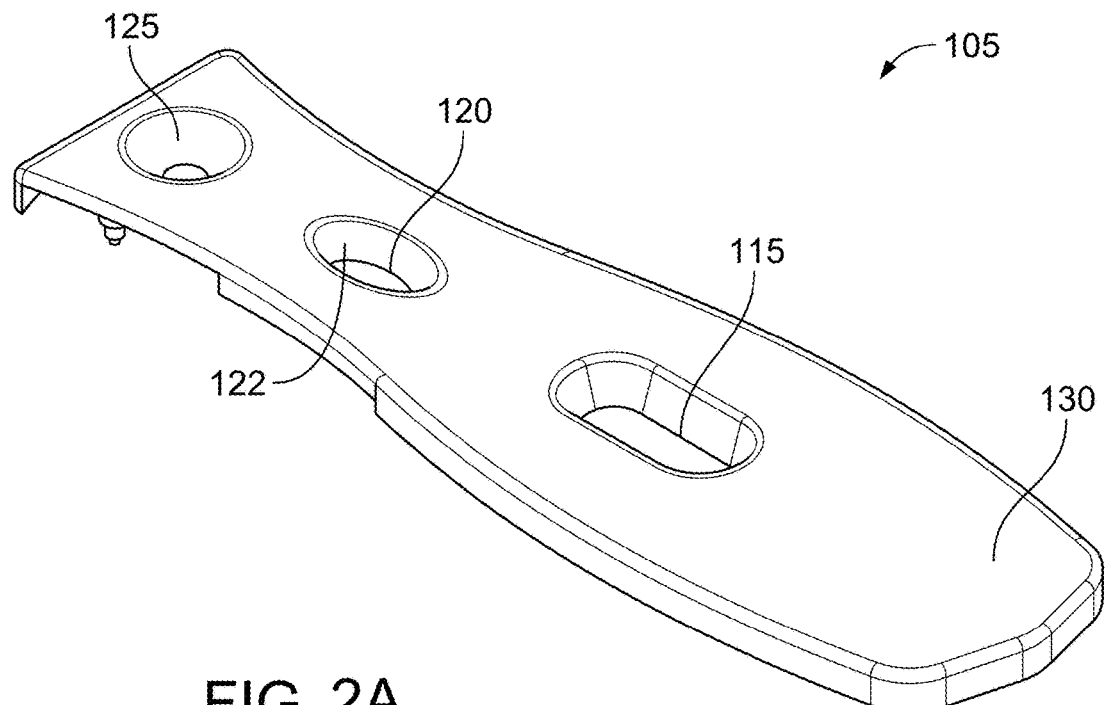
FIG. 2A is a top perspective view of one example of a top portion of the ST2 detection apparatus of FIG. 1.
Figure 2B:
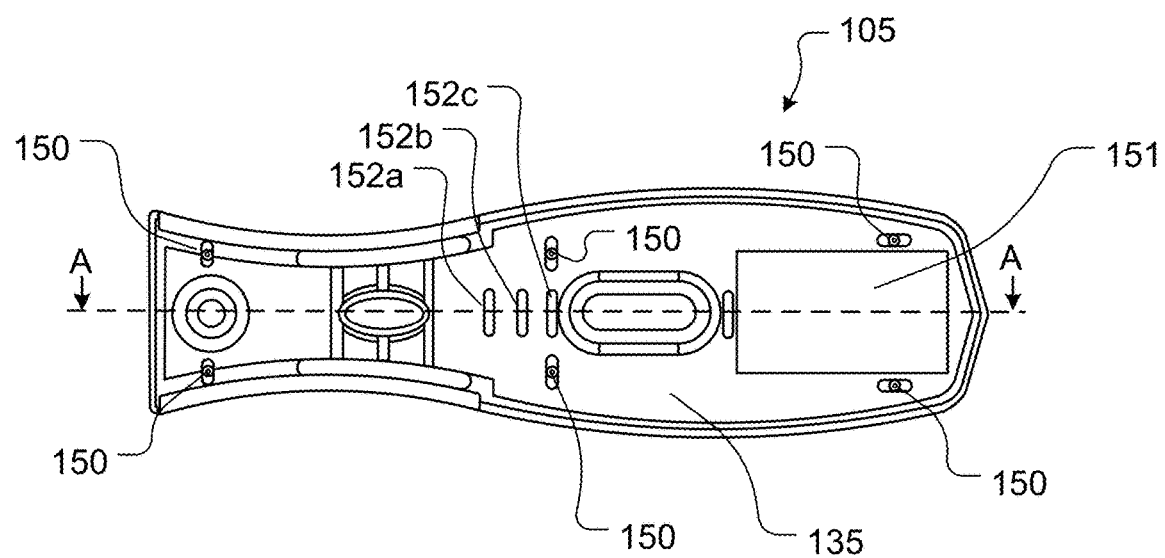
FIG. 2B is a view of the inner face of the top portion shown in FIG. 2A.

FIGS. 2A-2E show construction details of a particular implementation of the top portion 105. FIG. 2A shows the outer face 130 of the top portion 105, and FIG. 2B shows the inner face 135 of the top portion 105. In some implementations, the inner face 135 (that faces the inner face of the bottom portion 110) can include multiple mating projections 150 that are configured to couple with corresponding receptacles in the bottom portion 110. The example of FIG. 2B shows six such mating projections 150. Other implementations may have a different number of such mating projections 150. The mating projections couple with the corresponding receptacles in the bottom portion 110 such that the top and bottom portions together form a substantially sealed housing or cassette in which the test strip is disposed. For this reason, the mating projections 150 can be referred to as attachment projections, and the corresponding receptacles can be referred to as attachment receptacles.

In some implementations, the inner face 135 of the top portion 105 includes multiple projections 152a, 152b, and 152c (152, in general). In some implementations, the projections can be in the form of ridges. The dimensions of the projections 152 are different from one another, and are configured in accordance with the varying thickness of the test strip housed within the cassette. In some implementations, the test strip is thicker in the portion that comes in contact with projection 152a than the portions that come in contact with portions 152b and 152c, respectively. Accordingly, the height of the projections 152 from the inner face 135 can be adjusted such that projection 152a is shorter than projection 152b, and projection 152b is shorter than projection 152c. The respective height of each projection 152 is configured such that when the top portion 105 is coupled with the bottom portion 110 to form a cassette, each of the projections 152 is in contact with the test strip housed within the cassette. Further, the set of projections 152 are configured such that they produce a pressure gradient within the test strip to allow a sample fluid to flow at a predetermined flow rate along the length of the test strip between the projection 152a and the projection 152c. In some implementations, the set of projections 152 can be configured to support the test strip without creating a pressure point that hinders the flow rate along the length of the test strip. In some implementations, the projections can be measured with respect to a baseline such as the line 153. In the example of FIG. 2E, the heights of the projections 152a, 152b, and 152c are 0.003 units, 0.011 units, and 0.027 units, respectively. The flow rate can also be configured, for example, by varying various parameters of the test strip, including, for example, composition of conjugates disposed in the test strip.

Other variations of the top portion are also possible. FIGS. 2C and 2D show the side view and the inside face 136, respectively, of an example of such a variation 106. The top portion 106 shown in FIGS. 2C and 2D, can be used, for example, in an implementation where the cassette is used in conjunction with a reader device such as the one described below with reference to FIGS. 7A-7C. In some implementations, where the cassette is used in conjunction with a reader device, plasma (and not whole blood) can be used as the test specimen or sample, and the flow dynamics can be different from implementations that use whole blood as the sample. Accordingly, the sample port 121 of the top portion 106 (FIG. 2D) can be made smaller than the sample port 120 of the top portion 105 (FIG. 2B), where a larger port may be needed to facilitate an appropriate flow for separating plasma from the whole blood sample.

In some implementations, the top portion 105 and the bottom portion 110 also enclose an identification tag (such as a radio frequency identification (RFID) tag) that includes identification information about a corresponding patient and/or sample. In such cases the top portion 105 may have a particular portion 151 configured for receiving the identification tag. In some implementations, the identification information can also be encoded, for example, as a barcode or quick recognition (QR) code, and printed on an exterior face of the top portion or the bottom portion. The identification tag or code can be scanned or detected by an appropriate reader to automatically determined identification information related to a patient or sample.

FIG. 2E shows a cross sectional view of the top portion 105, together with a blown-up view of the projections 152. As shown in FIG. 2E, the height of the projection 152b is more than that of the projections 152a, and the height of the projection 152c is more than that of the projections 152b. In the example shown in FIG. 2E, to achieve the desired pressure gradient within a test strip in the cassette, a proportion of the heights of the projections 152a, 152b, and 152c from a reference level 155 is 3:11:27. In some implementations, the test strip disposed within the cassette may have a limited range of pressure tolerance against leakage. For example, if the fit is too tight, portions of the test strip may be crushed thereby resulting in leakage of test fluid from the strip. On the other hand, if the fit is too loose, there may be leakage too. In some implementations, the heights of the projections 152a, 152b, and 152c can be configured such that the test strip is held within the cassette without breaching the corresponding pressure tolerance range. This can prevent leakage from the test strip disposed within the cassette.

Figure 3A:
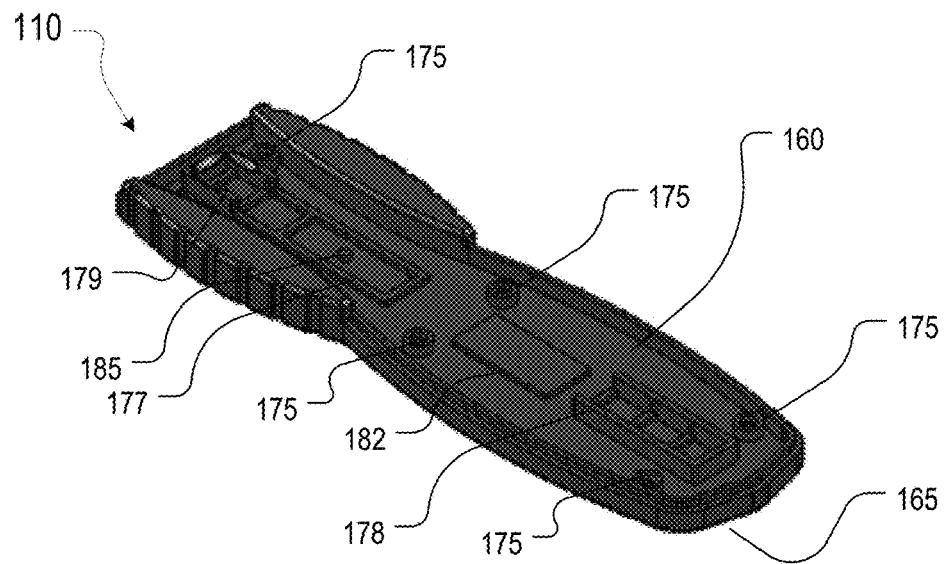
FIG. 3A is a perspective view of the inner face of an example of a bottom portion of the ST2 detection apparatus of claim 1.
Figure 3B:
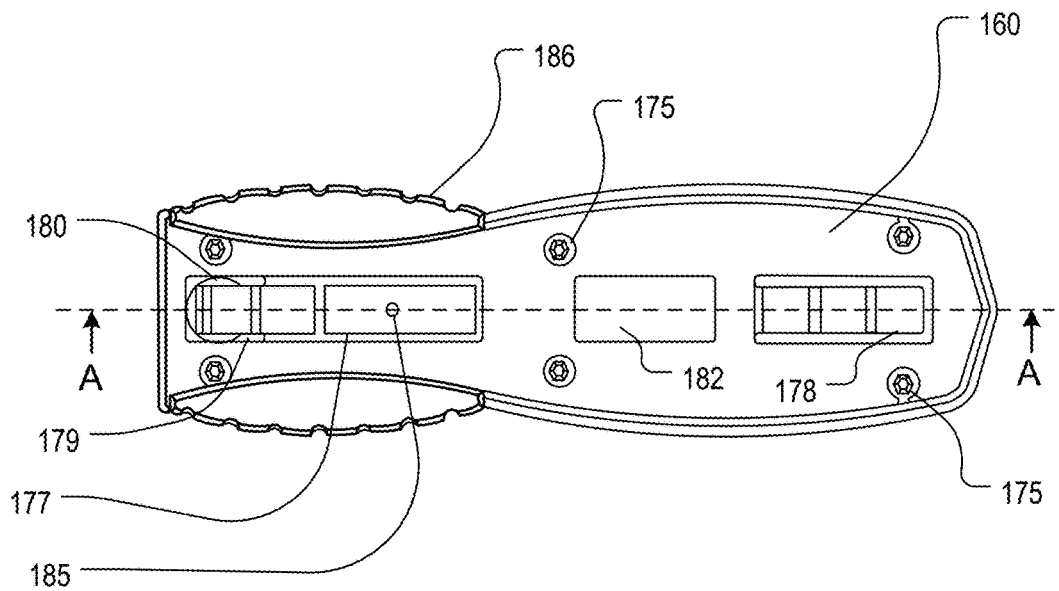
FIG. 3B is a top view of the inner face of the bottom portion shown in FIG. 3A.
Figure 3C:
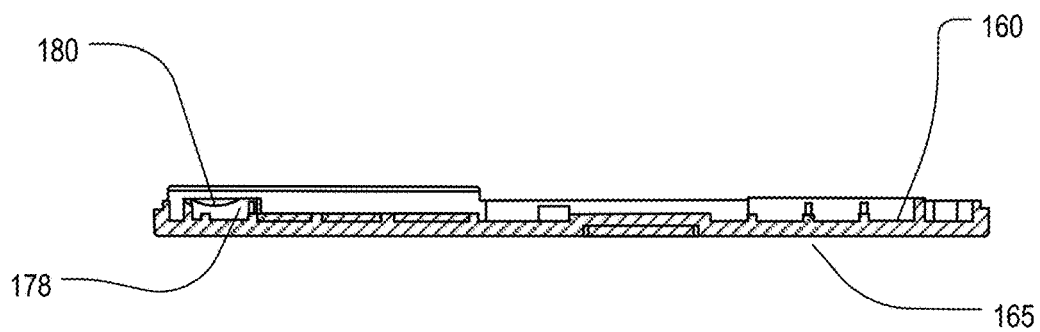
FIG. 3C is a side view of the inner face of the bottom portion shown in FIG. 3A.

FIGS. 3A-3C show construction details of the bottom portion 110 of the apparatus 100. FIG. 3A shows a perspective view in which the inner face 160 of the bottom portion is visible. When the bottom portion 110 is attached to the top portion 105, the inner face 160 faces the inner face 135 of the top portion 105. As shown in FIG. 3C, the outer face 165 is on the opposite surface of the bottom portion 110, and is not visible in the view shown in FIG. 3A. The inner face 160 includes multiple receptacles 175 that are configured to couple with the mating projections 150 disposed on the inner face 135 of the top portion to form the cassette that houses the test strip. In some implementations, the receptacles 175 are circular, and the inner diameters of the receptacles 175 are marginally smaller than the diameters of the corresponding mating projections 150. In the example shown, the inner diameter of the receptacles are 0.047 units, whereas the diameter of the mating projections are 0.05 units (see FIG.

2B). This allows for a tight coupling between the mating projections and the corresponding receptacles.

As shown in FIG. 3B, the inner face 160 includes a first channel 177 and a second channel 178 that together support the test strip within the cassette. In some implementations, the first channel 177 includes a raised portion 179 that has a groove 180 that forms a sealing configuration with the buffer port 125 of the top portion 105. In some implementations, the inner face 160 of the bottom portion 110 can also be configured to include one or more supporting portions for supporting the test strip. For example, the inner face 160 of the bottom portion 110 can include one or more supporting platforms 182. In some implementations, the first channel 177 and/or the second channel 178 can be configured to include one or more supporting projections (e.g., the supporting projection 185 in the first channel 177) to support the test strip. The bottom portion 110 can also include a grip 186 for holding the cassette. In some implementations, the grip 186 can be corrugated to reduce the chance that the cassette will slip from a person's hand.

Figure 4A:
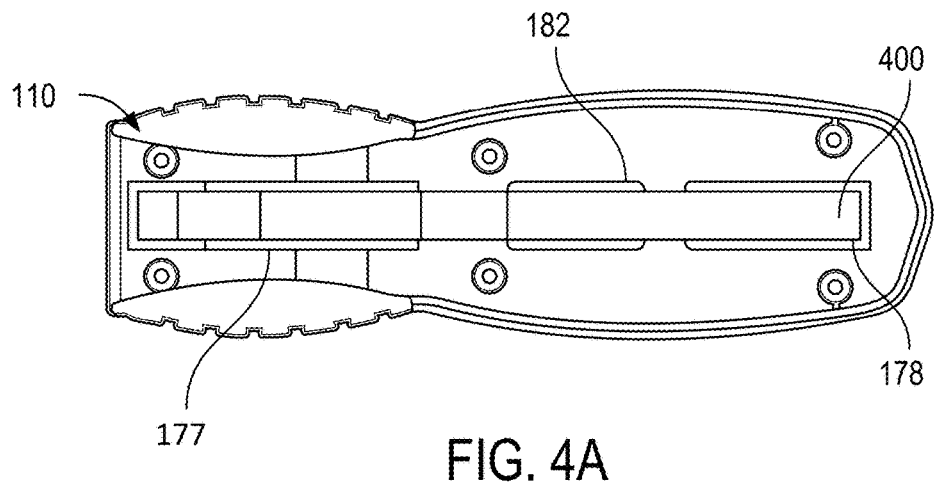
FIG. 4A is a schematic that shows an example of an ST2 test strip positioned in the bottom portion of the ST2 detection apparatus of FIG. 1.

FIG. 4A shows an example of a ST2 test strip positioned in the bottom portion 110 of the apparatus 100. In the example shown in FIG. 4A, the test strip is supported by the first channel 177, the second channel 178, and the supporting structure 182. Various types of test strips can be used in the apparatus 100. Two examples of such test strips are described below with reference to FIGS. 4B and 4C.

Figure 4B:
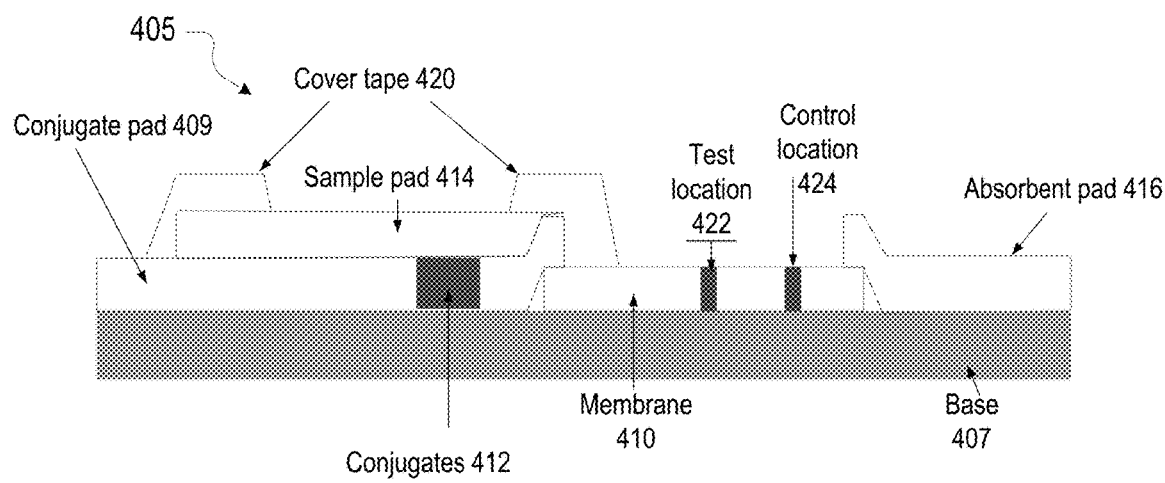
FIG. 4B is a schematic diagram showing construction details of one example of a test strip.

FIG. 4B shows the construction details of an example of a test strip 405. The test strip 405 can include a base 407 that provides structural support. For example, the base can be constructed from an 80 mm thick lamina (e.g., made of plastic, e.g., polyvinyl chloride (PVC), polystyrene, polyester, or biodegradable plastic such as celluloid) on which the other portions of the test strip are laminated. The test strip includes a conjugate pad 409 and a membrane 410. The conjugate pad 409 and the membrane 410 are disposed on the base 407 such that the membrane 410 is in fluid communication with the conjugate pad 409. The conjugate pad 409 can be composed of an absorbent filtration media (e.g., a 38 mm Grade 8964 pad manufactured by Ahlstrom Corporation). In some implementations, the conjugate pad can include glass and/or polyester fibers. The conjugate pad 409 includes one or more conjugates 412 that bind with ST2 present in a body fluid (e.g., plasma) to produce conjugate-ST2 complexes. The conjugates can include, for example, a reporter group bound to antibodies that bind to ST2. In some implementations, the antibodies that bind to ST2 can include monoclonal antibodies such as 7E4 or 9F8-monoclonal-anti-ST2 antibodies.

The reporter group can include, for example, gold particles, and in such cases the antibodies are conjugated to colloidal gold. The reporter group can also include fluorescent particles (e.g., fluorophores such as fluorescein, rhodamine, or eosin) for implementations in which a fluorescent assay is used. As one particular example, the 7E4 monoclonal anti-ST2 antibody can be conjugated to 40 nM colloidal gold at 0.010 mg/ml of 1 OD colloidal gold. As another particular example, the 9F8 antibody can be conjugated to gold or fluorescent particles for use in a fluorescent assay.

In some implementations, the conjugate pad may be pre-treated to include a conjugate block buffer. The conjugate block buffer includes a buffering agent, such as borate or N-(2-Acetamido)-2-aminoethanesulfonic acid (ACES), Tris-HCL, Tris-base, 3-(N-morpholino)propanesulfonic acid (MOPS), phosphate buffered saline (PBS), and a blocking agent (e.g., bovine serum albumin (BSA), casein, Fish Gelatin, Polyethylene glycol (PEG), Polyvinyl alcohol (PVA), Polyvinylpyrrolidone (PVP), Polyacrylic acid (PAA), Polyacrylic maleic acid (PAMA) to block non-specific binding of the antibodies used in the test assay.

In on example, the conjugate block buffer can include, for example, a solution of 50 mM Borate at 10% Bovine Serum Albumin (BSA) and having pH=9.0. In another example, the conjugate block buffer can include a solution of 100 mM ACES, 25 mM NaCl, 75 mM $MgCl_2$, at 3% BSA, 1% Polyvinylpyrrolidone (ave. MW 40K) (PVP-40), 0.25% Triton X-100, pH 6.5. In yet another example, the conjugate block buffer can include a solution of 10 mM Borate, 3% BSA, 0.25% PVP-40, 0.25% Triton X-100, pH=8.0. In some implementations, a conjugate diluent of 50 mM Borate at 1% BSA, and having a pH=9.0 can also be used.

The conjugate can be pre-treated to include the conjugate block buffer by dipping and soaking the conjugate pad in the conjugate block buffer for a period of time (e.g., two minutes). The excess buffer can then be removed from the conjugate pad, for example, by placing the conjugate pad between layers of absorbent material (e.g., paper towels) and applying pressure. The wet conjugate pads can then be dried (e.g., at 37° C. for one hour) and stored desiccated (<20% RH) at room temperature.

The conjugates 412 can be added to the conjugate pad 409, for example, by spraying the conjugate pad with a solution including the conjugates. The conjugate pad 409 is then dried (e.g., in a 37° C. forced air oven for one hour) and stored desiccated (<20% RH) at room temperature. The conjugate pad 409 can be trimmed to the appropriate size and laminated onto the base 407.

The solution including the conjugates that is used for spraying the conjugate pad 409 can be prepared in various ways. In general terms the process is as follows. First, the antibody is dialyzed, e.g., with 10 mM phosphate (pH ~7.3), and an effective amount of the reporter group, e.g., 40 nm colloidal gold, is adjusted to a relatively neutral pH, e.g., from about 5.0 to about 10.0, e.g., 6.5 to 9.5, e.g., the pH can be 7.0, using a buffering agent, e.g., as noted above, e.g., 0.2 M $K_2CO_3$. An effective amount of the antibodies, e.g., 10 μg of the antibody, is then added to an amount of the reporter group mixture, e.g., 1 ml of colloidal gold, and the solution is mixed for a time sufficient to thoroughly mix all the components, e.g., for 15 minutes at room temperature. Then the blocking agent is added, e.g., 10% BSA in a buffering agent, e.g., 50 mM borate (pH ~9.0) using 10% of the volume of the reporter group, e.g., colloidal gold, used, and the solution is mixed again, e.g., for 30 minutes at room temperature. The solution is then centrifuged for about 30 minutes at 14,000×G to form a pellet of the components that have not dissolved. After the supernatant is removed and discarded, the pellet is re-suspended in a conjugate diluent and an appropriate amount is added to reach a target optical density (OD). In some cases, a sugar, e.g., sucrose and/or trehalose can be added to the gold conjugate in appropriate amounts (e.g., 20% and 5%, respectively) and mixed until dissolved.

In some implementations, the test strip can also include a sample pad 414 on which the sample (e.g., whole blood) is dispensed. The sample pad 414 can be disposed over the conjugate pad 409, and can be configured to allow a part of the sample to pass through on to the conjugate pad 409. For example, if the sample used for the test strip is whole blood, the sample pad 414 can be configured to allow blood plasma to pass through while blocking other constituents of the blood. For this reason, the sample pad 414 can also be sometimes referred to as a plasma separation pad. In some implementations, a plasma separation membrane such as the Vivid™ plasma separation membrane manufactured by Pall Corporation can be used as the sample pad 414.

In operation, a sample (e.g., plasma) received within the conjugate pad 409 flows from the conjugate pad 409 to the membrane 410 and traverses the length of the membrane 410. The test strip 405 also includes an absorbent pad 416 (sometimes also referred to as a wick pad) for collecting the residual sample coming out of the membrane. In some implementations, a CO95 pad manufactured by EMD Millipore Corporation can be used as the absorbent pad 416. In other implementations, a CO83 pad, also manufactured by EMD Millipore Corporation, can be used as the absorbent pad 416. The absorbent pad 416 and the conjugate pad 409 are disposed at opposite ends (along the length) of the membrane 410.

Various combinations of the constituent parts described above can be used in constructing the test strip. For example, to construct the test strip 405 shown in FIG. 4B, the membrane 410 is laminated over the base 407. A CO83 absorbent pad 416 (e.g., a 21 mm or 25 mm wicking pad) can then be placed at one end of the backing card with an overlap (e.g., a 2 mm overlap) with the membrane 410. The conjugate pad 409 (e.g., a 36 mm or 38 mm conjugate pad) is laminated onto the base 407 overlapping the membrane by a short distance to ensure a good contact, e.g., 2 mm. The sample pad 414 (e.g., a 26 mm Vivid™ blood separation pad) is then laminated on top of the conjugate pad 409. Two strips of cover tape 420 can then be placed at both ends of the sample pad 414 such that one strip of the cover tape overlaps the membrane and the other strip of the cover tape overlaps the conjugate pad. The sheet thus prepared can then be cut into strips that fit the channel within the cassette.

Figure 4C:
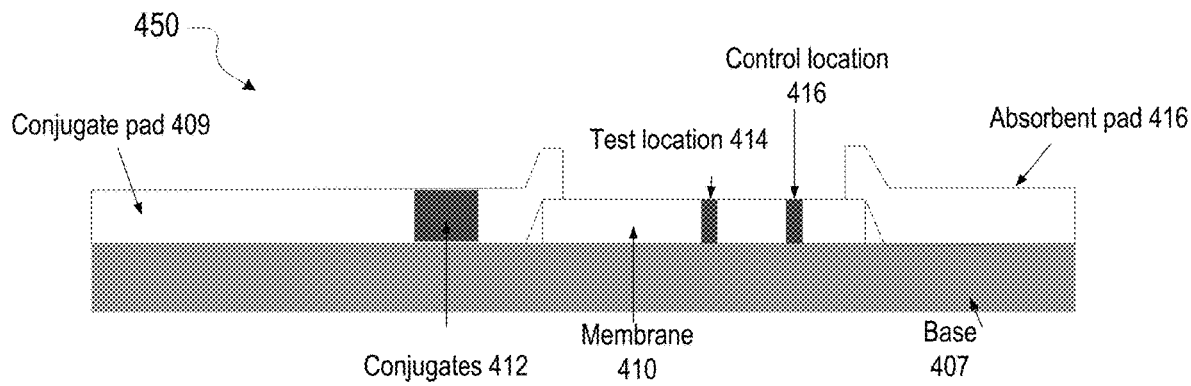
FIG. 4C is a schematic diagram showing construction details of another example of a test strip.

In some implementations, the test strip does not include a sample pad. An example of such a test strip 450 is shown in FIG. 4C. To construct the test strip 450, the process followed can be substantially similar to the one followed for constructing the test strip 405, with the exception that no sample pad or cover tapes are used. The test strip 450 can also be used as dipsticks.

In both test strips 405 and 450, the ST2 detection assay is carried out on the membrane 410. In some implementations, a nitrocellulose membrane (e.g., HF135 manufactured by EMD Millipore Corporation) can be used as the membrane 410. The membrane 410 includes a test location 422 and a control location 424. The test location 422 includes an antibody that binds specifically to any ST2 in the sample, such as 7E4 or 9F8 monoclonal anti-ST2 antibodies at a predetermined concentration (e.g., 0.75 mg/mL, 1 mg/mL, 1.5 mg/mL, or 2.0 mg/mL). The control location includes another antibody that binds specifically to some component of the conjugate, such as the anti-ST2 antibody, which can be bound by a goat anti-mouse IgG at a predetermined concentration (e.g., 2.0 mg/mL, 0.5 mg/mL, or 0.125 mg/mL). The test location 422 and the control location 424 are striped onto the membrane using, e.g., a frontline dispenser and at a predetermined dispense rate (e.g., 1 µL/cm). The membrane is then dried and stored desiccated at room temperature.

In some implementations, the membrane 410 is pre-treated using a membrane blocking buffer. An example of a solution used as the membrane blocking buffer is 100 mM Sodium Phosphate, 0.1% Sucrose, 0.1% BSA, and 0.2% PVP-40, at pH 7.2. Other blocking agents are known and can be used. Examples of such blocking agents include bovine serum albumin (BSA) and casein, dry milk, fish skin gelatin, and polyethylene glycol (PEG). To pre-treat the membrane, the membrane 410 can be slowly dipped into the membrane blocking buffer and allowed to wick across the membrane 410. Excess buffer can be blotted off the top of the membrane 410, for example, using a paper or cloth, e.g., a Kimwipe™. The membrane 410 can then be dried (e.g., at 37° C. for 30 minutes), removed, and stored desiccated (<20% RH) at room temperature until used.

Figure 5A:
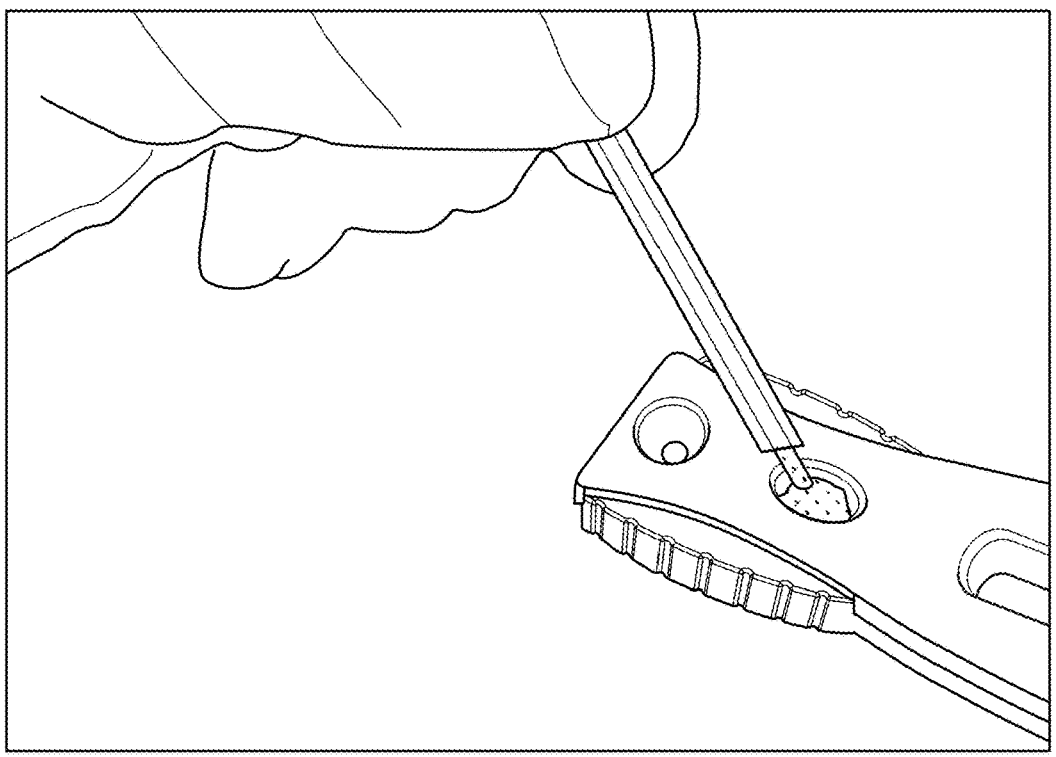
FIG. 5A is a photo that illustrates the application of a blood sample to the apparatus of FIG. 1.
Figure 5B:
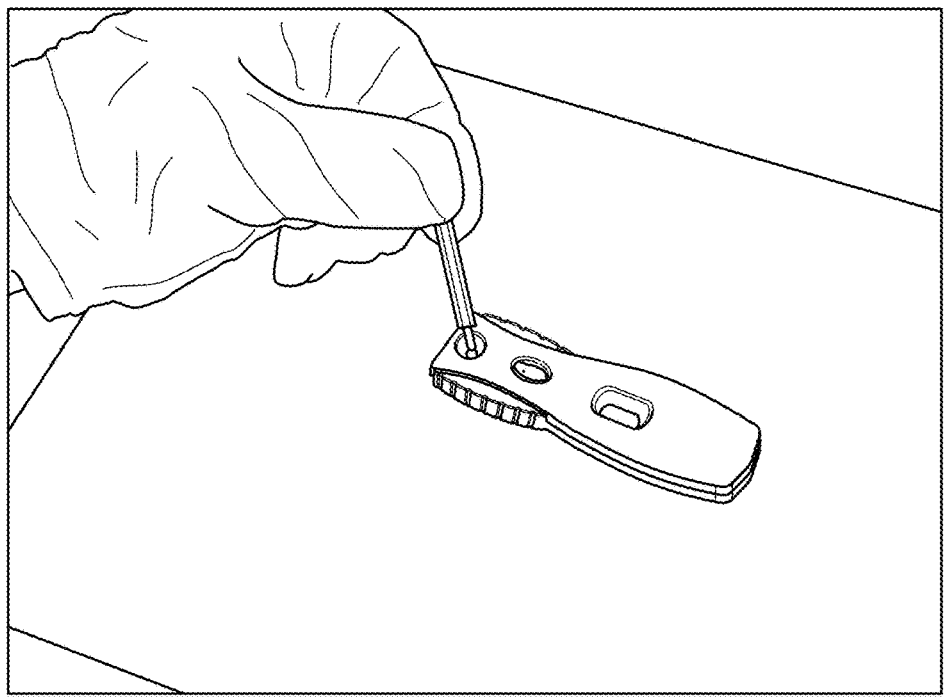
FIG. 5B is a photo that illustrates the application of a buffer solution to the apparatus of FIG. 1.

To perform a test using the apparatus 100 described above, a test strip (e.g., the test strip 405) can be placed within the apparatus 100 and a predetermined amount of test fluid (e.g., blood or plasma) is dispensed into the sample port 120. This is shown in FIG. 5A. In general, commercial cassettes will be preloaded with the appropriate test strip. For example, 40 µl of blood or 30 µl of plasma can be dispensed into the sample port 120 using a pipette, as shown in FIG. 5A. In some implementations, the sample may be pre-treated with a human anti-mouse antibody (HAMA) blocker. After waiting for a predetermined time period (e.g., about 1 minute) for the sample to soak in, a running buffer is dispensed into the buffer port 125. This is shown in FIG. 5B. For 40 µl of blood or 30 µl of plasma, about 120 µl of the running buffer may be dispensed into the buffer port 125. In some implementations, the conjugate 412 (as shown in FIG. 4B) is not already present within the conjugate pad 409, and is also dispensed into the buffer port 125. If the conjugate 412 is already present within the conjugate pad 409, only the running buffer is dispensed into the buffer port 125. Within the conjugate pad 409, the ST2 in the sample binds with the conjugate 412 to produce conjugate-ST2 complexes. These conjugate-ST2 complexes traverse the conjugate pad 409 and the membrane 410 and get bound to antibodies in the control location 424. If the level of ST2 in the sample is above a threshold, not all of the ST2 is bound to the conjugate 412. The unbound ST2 traverses the conjugate pad 409 and the membrane 410 where they get bound to the antibodies at the test location 422.

The strip is read or otherwise evaluated after another predetermined time period (e.g., about 5 to 25 minutes, e.g., 10 to 20 minutes, e.g., 15 minutes). If a fluorescent assay is used, the test strip can be evaluated using a fluorescence reader, e.g., an ESE Fluorescent Reader. If a gold assay is used, the test results are visually inspected and subjectively graded using, for example, a scale calibrated to the specific test.

The running buffer dispensed into the buffer port 125 is formulated to facilitate and/or expedite the flow of the sample (e.g., plasma) through the conjugate pad 409 and the membrane 410. The running buffer generally includes a buffering agent such as N-(2-Acetamido)-2-aminoethanesulfonic acid (ACES), together with other components (e.g., detergents such as Tween-20 and Triton X-100). One example composition for the running buffer can be 100 mM ACES, a salt solution that can be used to achieve a desirable ionic composition of the buffer (e.g., 100 mM Magnesium Chloride), 0.1% Tween-20, 0.05% Proclin 300, with pH about 6.5.

Figure 6A:
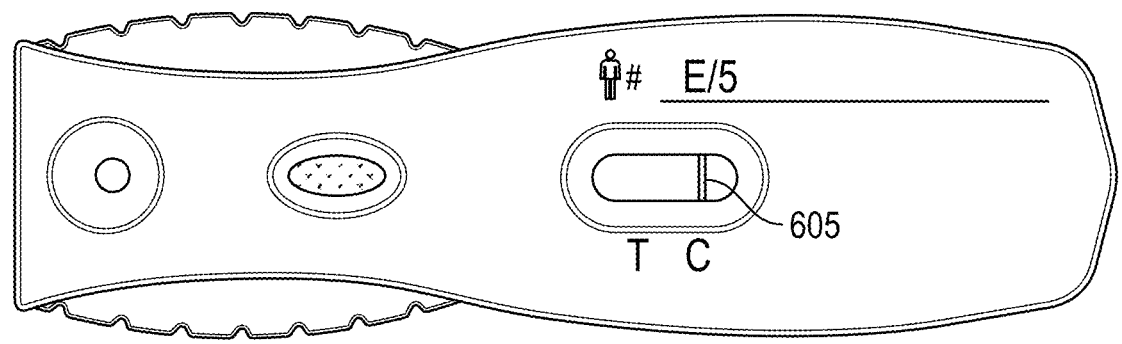
FIG. 6A is a photo that shows an example of a test result in which a control line can be seen, but no test line is visible.
Figure 6B:
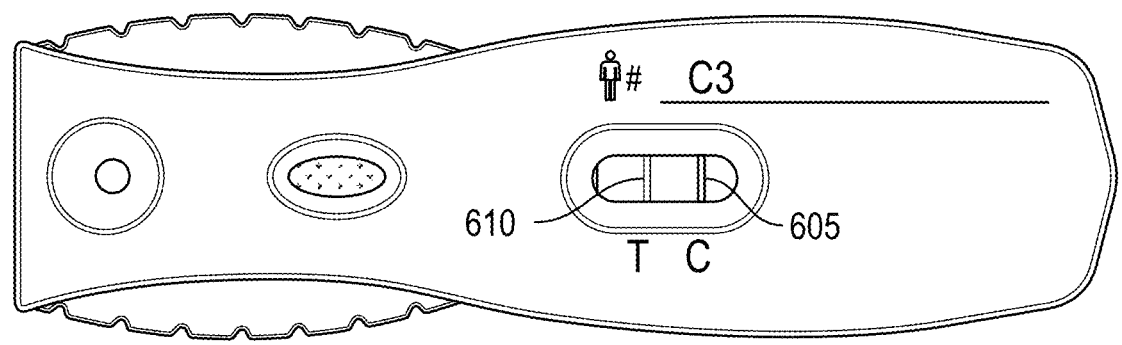
FIG. 6B is a photo that shows an example of a test result that shows a control line and a faint test line.
Figure 6C:
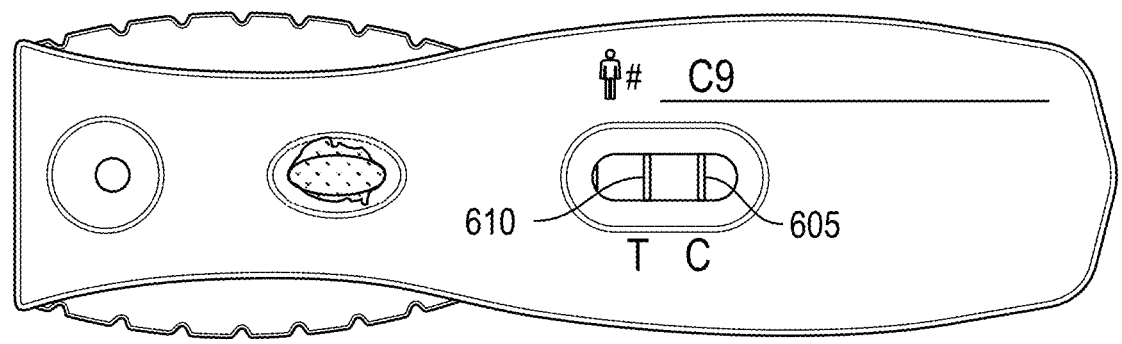
FIG. 6C is a photo that shows an example of a test result that shows a clearly visible control line and a clearly visible test line.

FIGS. 6A-6C show examples of test results that are visually inspected to determine the presence or absence of ST2 in the sample. FIG. 6A shows a result in which the control line 605 can be seen (therefore indicating that the test was successfully completed), but no test line is visible. Such absence of a visible test line may indicate that the level of ST2 is below the cutoff level (e.g., 35 ng/mL) that the apparatus is configured to detect. FIG. 6B shows the control line 605, and a faint test line 610. The faint test line 610 can indicate that the level of ST2 in the corresponding sample is close to the cutoff level but significantly above the cutoff level. FIG. 6C shows a clearly visible control line 605 and a clearly visible test line 610. The clear test line 610 indicates that the level of ST2 in the corresponding sample is above the cutoff level.

Figure 7A:
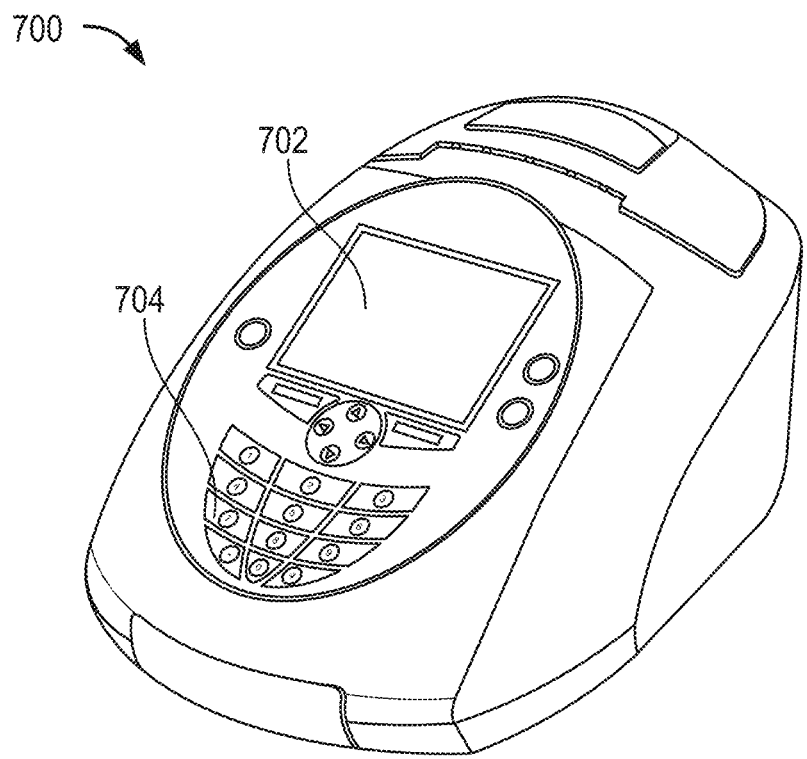
FIG. 7A is a view of the front of a reader device used in analyzing test results using ST2 test strips.
Figure 7B:
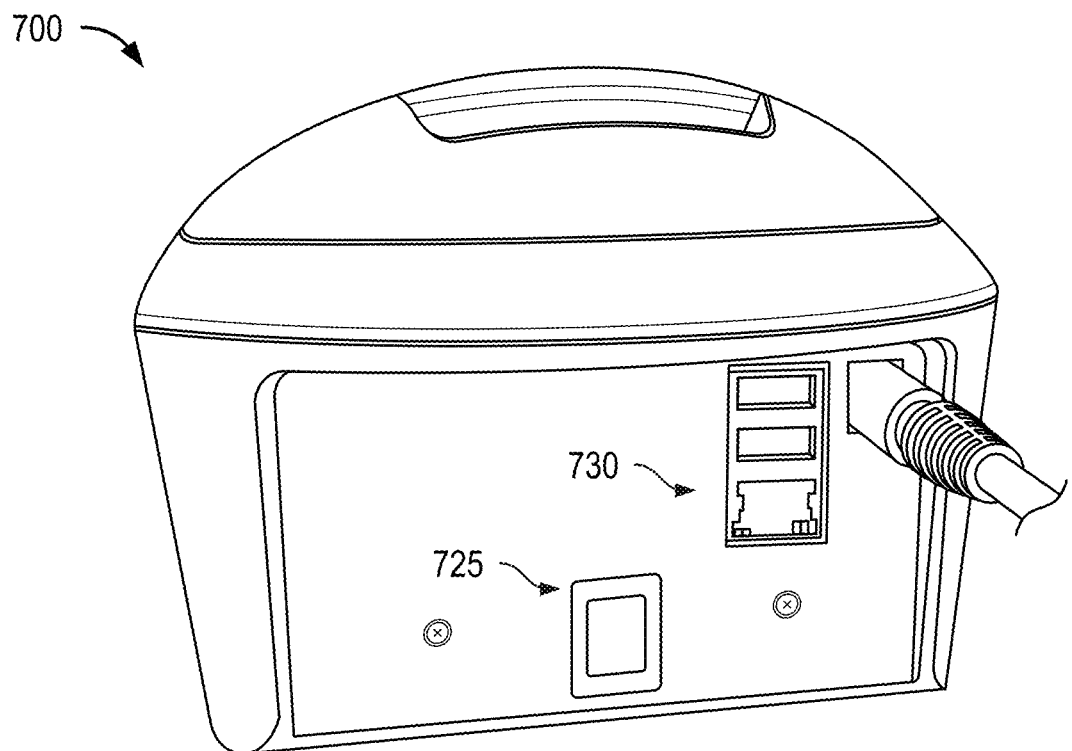
FIG. 7B is a view of the back of a reader device of FIG. 7A.
Figure 7C:
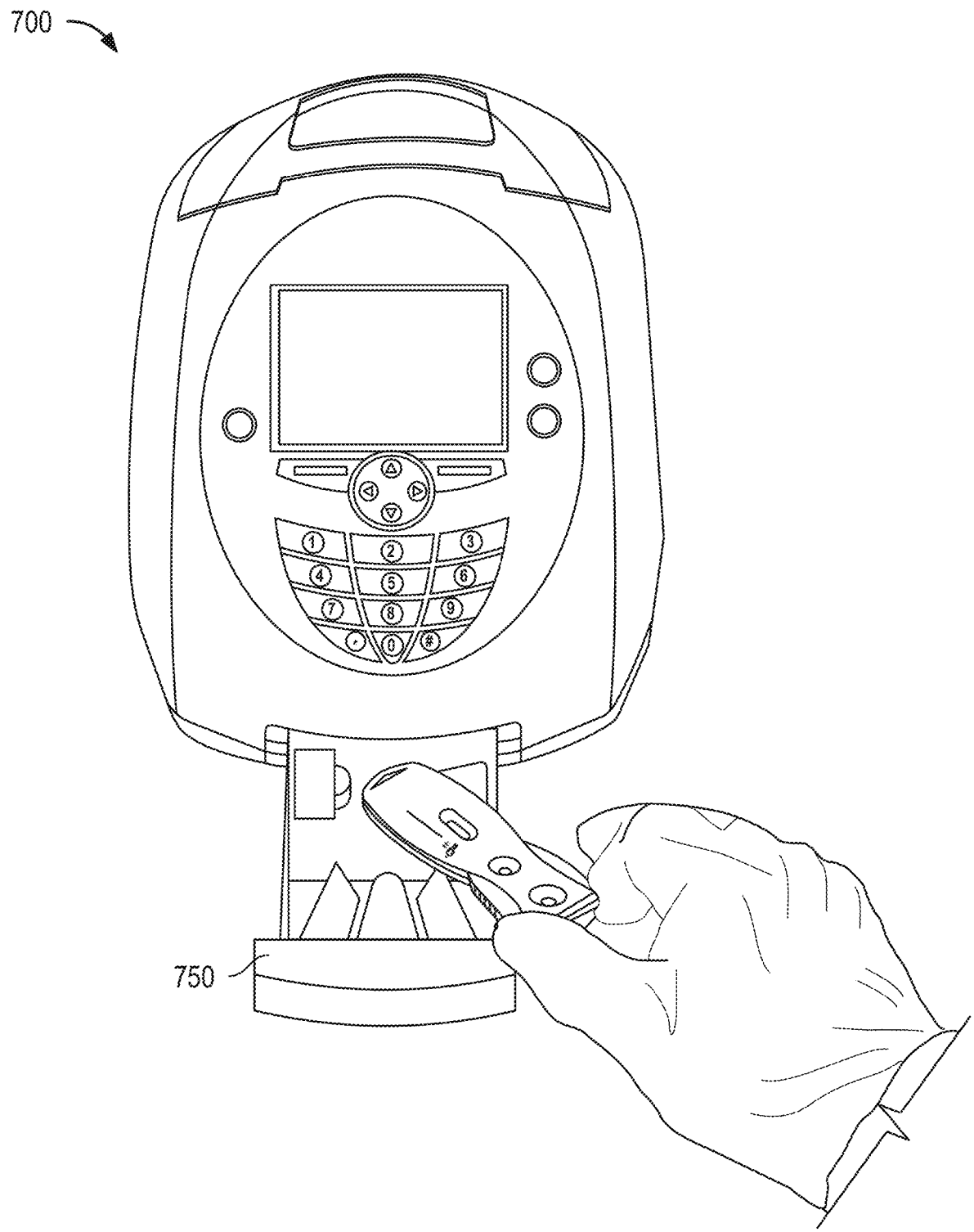
FIG. 7C is a top view of the reader device of FIG. 7A in operation.

In some implementations, a reader device can be used for analyzing test results for tests performed using the ST2 test strips described above. FIGS. 7A and 7B show the front and back, respectively, of an example of such a reader device 700 developed by LRE Medical GmbH, Germany. The reader device 700 includes a power switch 725 and a receiving section 750 as shown in FIG. 7C. The receiving section 750 can be configured to accept at least a portion of the cassette or housing within which a test strip is disposed. For example, the receiving section 750 can include a slide-out section that accepts the cassette. In another example, the receiving section can include an opening through which a portion of the cassette is inserted into the reader device 700. In some implementations, the reader device 700 may be configured to initiate an analysis of the test strip automatically upon insertion of the cassette into the reader. The operation can also be controlled using a command provided via a user interface.

In some implementations, the reader device 700 can include, for example, an optical system for analyzing the amount of analyte in an ST2 test strip. For example, the reader device can include a fluorescence optical system configured for a particular operating range such as TF5 (i.e., excitation at ~650 nm and emission at ~670 nm) to quantitatively determine the amount of analyte present. The optical system may be optimized for the particular operating range, and/or the type of fluorescence that is to be analyzed. In some implementations, the reader device 700 can be made user-configurable, for example via a graphical user interface (GUI), to handle multiple different types of test cartridges with different assays.

In some implementations, the reader device 700 can include a display (e.g., a 3.5" LCD QVGA color graphic display with backlighting) and a keypad 704 for operating the device. The key pad 704 can include, for example, any combination of soft keys, functional keys (e.g., eject, main menu, paper feed), navigation keys (e.g., up, down, left, right), character keys, and numeric keys. The device 700 can also include one or more on-board controllers that schedule, manage, and drive various motors, actuators, sensors, etc. in order to analyze test strips and provide results. In some implementations, the GUI can be used for presenting one or more menu-driven interfaces to support one or more functions such as running tests, performing quality control, retrieval of stored results, querying databases, performing system checks, facilitating instrument setup, and facilitating assay development.

In some implementations, the reader device 700 can include an illumination optic system configured to emit electromagnetic radiation that impinges the portion of the test strip being evaluated. The reader device also includes a receiver optic system configured to detect portions of the electromagnetic energy reflected, refracted, absorbed, emitted, and/or transmitted through the test strip. In some implementations, the reader device 700 can include a camera module for capturing image information pertaining to the portion of the test strip being evaluated. The reader device 700 can also include one or more processors for analyzing the information obtained by the illumination optic system, receiver optic system, and/or the camera module. In some implementations, the reader device 700 can also include an identification module (e.g., an RFID tag reader, or barcode reader) to automatically determine identification information from the cassette or housing inserted into the housing.

The reader 700 can also include one or more of an acoustic output device (e.g., a speaker), an internal printer (e.g., for printing results), a temperature sensor, a data storage device (e.g., random access memory, hard disk etc.), and one or more communication ports. Examples of communication ports 730 are shown in FIG. 7B, and can include USB host interfaces (USBH), local area network (LAN) interface, PS2 interface, and USB device interface (USBD). The reader device 700 can also be configured to have wireless communications capabilities.

The information captured by the optic systems within the reader device 700 can be analyzed to obtain quantitative information on analytes within a test strip. For example, the information can be analyzed to determine a level of ST2 within a sample tested using the test strip. The analysis can be performed, for example, on board the reader device 700 using one or more processors of the device, or at a remote computing device with which the reader device 700 communicates.

The analysis can include various processes. In some implementations, the captured information can be analyzed to determine a level of darkness for the test line and/or the control line of the test strip, and the level of darkness is correlated to an amount of ST2 in the sample. In some implementations, the level of ST2 is determined using multiple test strips for analyzing the sample from the same individual.

In some implementations, for each run, the test strip is read multiple times, possibly at substantially periodic intervals. For example, for each run of a test, a corresponding test strip can be read once every minute ten times to obtain ten readings. Absolute differences can then be calculated between each pair of readings, and the results stored as an appropriate data structure such as a matrix. For the example of ten readings, the size of the matrix would be 10×10. The rows and columns of the matrix are then summed and the results sorted. The values that correspond to the smallest differences can then be selected for computing the representative level of darkness for the test strip. For example, five values corresponding to the smallest differences can be chosen and then averaged to determine the representative level of darkness used in determining the amount of ST2 in the corresponding sample.

Using the apparatus and test strips described herein, ST2 levels in the body can be easily and reliably determined. Such determination is beneficial at least because elevated concentrations of ST2 are markedly prognostic for death within one year, with a dramatic divergence in survival curves for those with elevated ST2 soon after presentation, regardless of the underlying diagnosis. As one example, there is a dramatic relationship between elevations of ST2 and the risk for mortality within one year following presentation with dyspnea. The relationship between ST2 and death in dyspneic patients can be independent of diagnosis, and supersede all other biomarker predictors of mortality, including other markers of inflammation, myonecrosis, renal dysfunction, and notably NT-proBNP, a marker recently described as having value for predicting death in this population (Januzzi et al., Arch. Intern. Med. 2006; 166(3):315-20). Indeed, most of the mortality in the study was concentrated among subjects with elevated ST2 levels at presentation; however, the combination of an elevated ST2 and NT-proBNP was associated with the highest rates of death within one year.

Elevated concentrations of ST2 can also be correlated with the presence of severe disease in a subject, regardless of the underlying cause of the disease. Therefore, for undiagnosed subjects, the apparatus described herein can be used to determine how aggressively a diagnosis should be sought. For example, a high ST2 level would indicate the presence of severe disease, and suggest that the subject should be treated as a high-risk case. For subjects with a known diagnosis, the apparatus described herein can be used to help determine the severity of the underlying pathology because a higher ST2 level is associated with more severe disease.

The test strip, and the apparatus in general can be used in assessing prognosis and monitoring the efficacy of treatment of various cardiovascular diseases. The use of ST2 as a marker for diseases has been described in the following U.S. patents and Published Applications, the contents of which are incorporated herein by reference: US 2009/0305265 (Snider et al.), US 2010/0009356 (Snider et al.), US 2011/0053170 (Snider et al.), U.S. Pat. No. 8,597,958 (Lee), U.S. Pat. No. 8,617,825 (Snider et al.), US 2014/0045200 (Snider et al.), US 2012/0065897 (Snider et al.), U.S. Pat. No. 7,432,060 (Lee), U.S. Pat. No. 7,655,415 (Lee), U.S. Pat. No. 7,670,769 (Lee), U.S. Pat. No. 7,985,558 (Lee), U.S. Pat. No. 8,420,785 (Snider et al.), US 2010/0055683 (Snider et al.), U.S. Pat. No. 8,530,173 (Lee), US 2013/0273562 (Lee), U.S. Pat. No. 8,734,769 (Lee), U.S. Pat. No. 7,989,210 (Lee), U.S. Pat. No. 7,998,683 (Snider et al.), U.S. Pat. No. 8,090,562 (Snider et al.), US 2013/0177931 (Snider et al.), US 2013/0244236 (Snider et al.), US 2012/0276551 (Snider), US 2014/0058743 (Snider et al.), US 2013/0071404 (Snider et al.), US 2013/0345805 (Snider et al.), U.S. application Ser. No. 14/244,526, filed Apr. 3, 2014 (Snider et al.), US 2014/0051773 (Snider), US 2012/0040381 (Snider et al.), U.S. application Ser. No. 14/267,487 (Snider), and US 2013/0317030 (Lee).

Other Embodiments

The foregoing description is intended to illustrate and not limit the scope of the appended claims. Other aspects, advantages, and modifications are within the scope of the following claims.

What is claimed is:

1. A test system comprising:
 a test strip;
 a housing for the test strip, wherein the housing comprises:
  a first section comprising an outer face and an inner face, wherein the inner face of the first section comprises a channel to receive the test strip along the length of the first section, and
  a second section configured to be attached to the first section such that in an attached configuration the inner face of the first section and the test strip received in the channel of the first section faces an inner face of the second section, wherein the second section comprises:
   a buffer port configured to allow a buffer solution to be dispensed to a portion of the test strip,
   a test window arranged such that one or both of a test location and a control location on the test strip are viewable through the test window in the attached configuration,
   a sample port disposed between the buffer port and the test window, and
   a set of projections disposed on the inner face of the second section between the test window and the sample port such that in the attached configuration, each projection in the set of projections is in contact with the test strip, wherein a height of at least one projection in the set of projections is different from a height of another projection in the set of projections, and heights of the different projections are configured such that, in the attached configuration, the set of projections produces a pressure gradient within the test strip that allows a fluid to flow at a predetermined flow rate along the length of the test strip between the first and last projections in the set of projections; and
 a reader device configured to accept at least a portion of the housing within the reader device, wherein the reader device comprises an optical system that captures one or more images of one or both of the test location and the control location on the test strip, and in response, displays a result based on analysis of the one or more images.

2. The test system of claim 1, further comprising an identification tag associated with the housing, wherein the reader device is configured to query the identification tag to obtain at least a portion of identification information about a patient or sample associated with the test strip.

3. The test system of claim 1, wherein the predetermined flow rate is such that the fluid flows from a portion of the test strip adjacent to the buffer port of the second section to a portion of the test strip adjacent to the test window of the second section in about 20 minutes.

4. The test system of claim 1, wherein the set of projections is a set of ridges.

5. The test system of claim 4, wherein the set of projections includes four ridges, a first ridge being disposed closer to the sample port than the other ridges, a fourth ridge being disposed closer to the test window than the other ridges, and a second ridge and a third ridge being disposed between the first and fourth ridges.

6. The test system of claim 1, wherein distances between projections in the set of projections are substantially equal.

7. The test system of claim 1, wherein the first section includes multiple attachment projections that are configured to attach to corresponding attachment receptacles disposed on the second section, wherein dimensions of the attachment projections and attachment receptacles are configured such that in the attached configuration, the set of projections produces the pressure gradient that allows the fluid to flow at the predetermined flow rate along the length of the test strip.

8. The test system of claim 1, wherein the test strip comprises:
 a base;
 a plurality of conjugates, each conjugate comprising a reporter group bound to a first antibody that binds to ST2;
 a conjugate pad disposed along a length of the base, wherein the conjugate pad includes the plurality of conjugates that bind with ST2 to produce conjugate-ST2 complexes, and wherein the conjugate pad is configured to receive a blood plasma sample;
 a plurality of second antibodies that bind to ST2;
 a plurality of third antibodies that bind to the conjugate-ST2 complexes; and
 a membrane disposed on the base such that the membrane is in fluid communication with the conjugate pad, wherein the plurality of second antibodies are bound to the membrane in a test location and the plurality of third antibodies are bound to the membrane in a control location arranged further from the conjugate pad than the test location.

9. The test system of claim 8, wherein either the first or the second antibodies bind specifically to ST2.

10. The test system of claim 8, wherein both the first and second antibodies bind specifically to ST2.

11. The test system of claim 8, further comprising an absorbent pad disposed on the base and in fluid communication with the membrane at an end or side of the membrane opposite the conjugate pad, wherein the absorbent pad is configured to absorb plasma and buffer that has traversed through the membrane.

12. The test system of claim 8, wherein the conjugate pad is disposed on the base to receive a buffer solution.

13. The test system of claim 8, wherein the conjugate pad comprises fibers comprising glass, polyester, or both glass and polyester.

14. The test system of claim 8, wherein at least one of the conjugate pad or the membrane comprises nitrocellulose.

15. The test system of claim 8, wherein the first antibodies are monoclonal antibodies.

16. The test system of claim 8, wherein the reporter group comprises fluorescent particles.

17. The test system of claim 8, wherein the third antibodies are goat anti-mouse IgG antibodies.

\* \* \* \* \*